United States Patent
Devos

(10) Patent No.: US 10,393,582 B2
(45) Date of Patent: Aug. 27, 2019

(54) METHOD FOR REFOCUSING AN OPTICAL ASSEMBLY

(71) Applicants: CENTRE NATIONAL DE LA RECHERCHE SCIENTIFIQUE, Paris (FR); UNIVERSITÉ DE LILLE 1, Villeneuve d'Ascq (FR); ISEN, Lille (FR)

(72) Inventor: Arnaud Devos, Ennetieres en Weppes (FR)

(73) Assignees: CENTRE NATIONAL DE LA RECHERCHE SCIENTIFIQUE, Paris (FR); UNIVERSITE DE LILLE 1, Villeneuve d'ASCA (FR); ISEN, Lille (FR)

( * ) Notice: Subject to any disclaimer, the term of this patent is extended or adjusted under 35 U.S.C. 154(b) by 0 days.

(21) Appl. No.: 15/539,476

(22) PCT Filed: Dec. 22, 2015

(86) PCT No.: PCT/EP2015/080932
§ 371 (c)(1),
(2) Date: Jun. 23, 2017

(87) PCT Pub. No.: WO2016/102540
PCT Pub. Date: Jun. 30, 2016

(65) Prior Publication Data
US 2017/0350757 A1    Dec. 7, 2017

(30) Foreign Application Priority Data

Dec. 23, 2014   (FR) ..................... 14 63250

(51) Int. Cl.
*G02B 21/24*    (2006.01)
*G01J 3/02*     (2006.01)
(Continued)

(52) U.S. Cl.
CPC ............. *G01J 3/027* (2013.01); *G01J 3/42* (2013.01); *G02B 7/28* (2013.01); *G02B 21/247* (2013.01);
(Continued)

(58) Field of Classification Search
CPC .. G01J 3/42; G01J 3/027; G02B 26/06; G02B 27/40; G02B 7/28; G02B 21/247
(Continued)

(56) References Cited

U.S. PATENT DOCUMENTS 6,747,736 B2 * 6/2004 Takahashi .......... G01N 21/3581
                                                356/319
6,844,963 B2 * 1/2005 Iketaki .................. G01J 3/4406
                                                250/458.1
(Continued)

FOREIGN PATENT DOCUMENTS

CA      02281747 A1    3/2000
FR       2887334 A1   12/2006
(Continued)

OTHER PUBLICATIONS

Jun. 13, 2016 International Search Report issued in International Patent Application No. PCT/EP2015/080932.
(Continued)

*Primary Examiner* — Isiaka O Akanbi
(74) *Attorney, Agent, or Firm* — Oliff PLC

(57) ABSTRACT

A method refocuses on an optical assembly target surface, using at least one beam originating from a short-pulse optical source, having at least one optical system for focusing the beam on the surface. Refocusing occurs after learning reference conditions for which the assembly is considered as focused. A focusing signal is detected representing a time overlap of pulses between a beam reflected and a reference beam not reflected by the surface, one of the (Continued)

Figure 1:
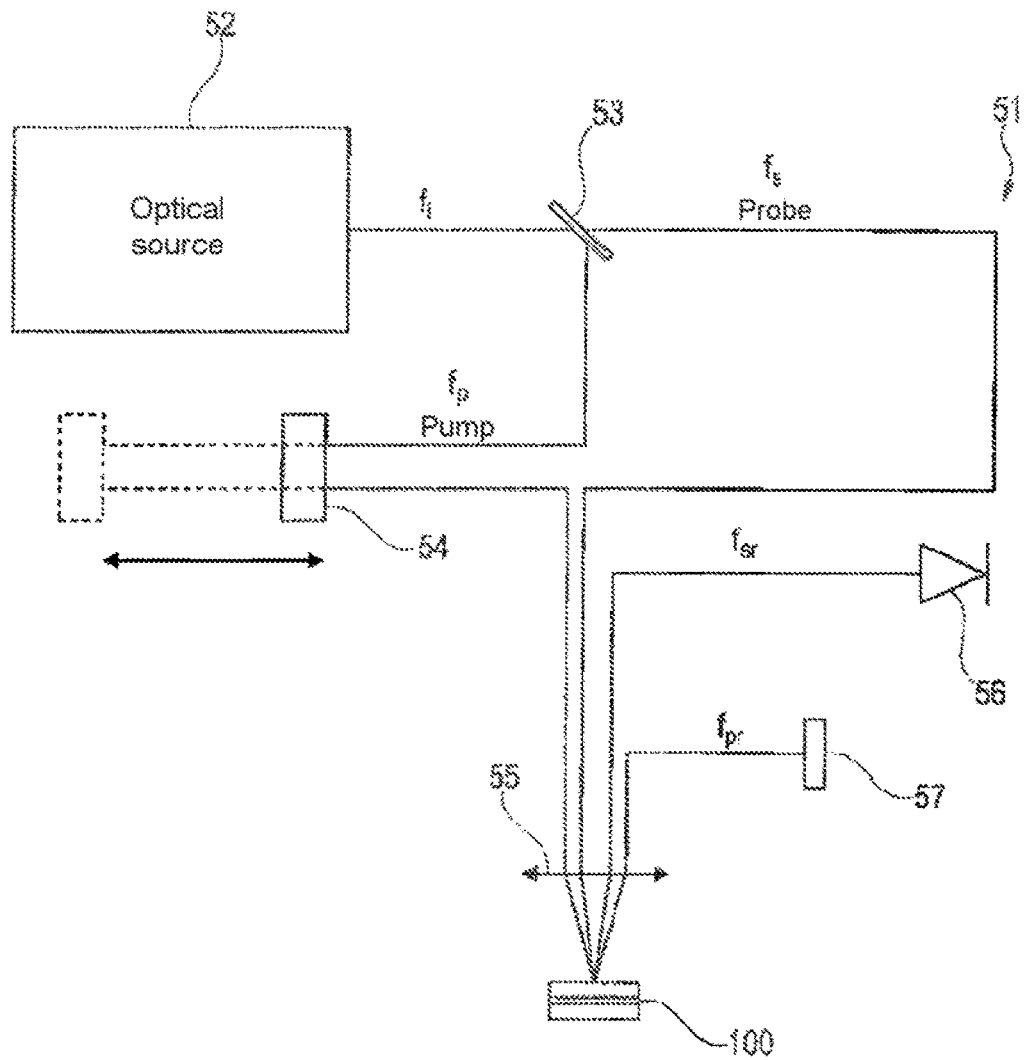

beams delayed by a delay line. The optical path on which the delay line is placed is varied, on the basis of the reference conditions, to cause the focusing signal to reach or exceed a predetermined threshold. The focus is adjusted on the basis of the path variation between the reference conditions and the conditions for which the focusing signal reaches or exceeds the threshold.

25 Claims, 5 Drawing Sheets

(51) Int. Cl.
*G01J 3/42* (2006.01)
*G02B 26/06* (2006.01)
*G02B 7/28* (2006.01)
*G02B 27/40* (2006.01)
*G01J 11/00* (2006.01)
*G01N 21/17* (2006.01)

(52) U.S. Cl.
CPC ............ *G02B 26/06* (2013.01); *G02B 27/40* (2013.01); *G01J 11/00* (2013.01); *G01N 21/1717* (2013.01)

(58) Field of Classification Search
USPC .............................. 356/237.5, 326, 602, 399
See application file for complete search history.

(56) References Cited

U.S. PATENT DOCUMENTS

| | | | |
|---|---|---|---|
| 7,355,702 B2* | 4/2008 | Yamashita | G01N 21/6458 356/301 |
| 7,633,043 B2* | 12/2009 | Ouchi | G01J 3/42 250/214.1 |
| 7,763,868 B2* | 7/2010 | Ouchi | G01N 21/3581 250/225 |
| 8,010,301 B2* | 8/2011 | Hlavaty | G01N 21/3563 250/341.8 |
| 8,213,022 B1* | 7/2012 | Riza | G01B 11/026 356/495 |
| 2005/0036136 A1 | 2/2005 | Opsal et al. | |
| 2007/0252984 A1* | 11/2007 | Van Beek | G01J 3/02 356/311 |
| 2008/0315131 A1 | 12/2008 | Devos et al. | |
| 2010/0090112 A1* | 4/2010 | Kawada | G01N 21/3581 250/338.4 |
| 2016/0011117 A1 | 1/2016 | Strola et al. | |

FOREIGN PATENT DOCUMENTS

FR 3001544 A1 8/2014
WO 2005/124423 A1 12/2005

OTHER PUBLICATIONS

Jun. 13, 2016 Written Opinion issued in International Patent Application No. PCT/EP2015/080932.

* cited by examiner

State of the Art

METHOD FOR REFOCUSING AN OPTICAL ASSEMBLY

The present invention relates to a method and a device for refocusing an optical setup.

Some optical setups using a beam originating from an optical source with temporally ultra-short pulses, that is to say of the order of the femtosecond or of the picosecond, are used in industrial machining, in order to accurately indicate the point of the piece to be machined.

In a so-called "time-resolved" optical setup, notably of the "pump-probe" type, temporally ultra-short laser pulses are used to optically excite the sample and detect its state before, during and after the creation of the phenomenon. It may involve exciting charge carriers in a metal or a semiconductor, adding heat or even generating acoustic pulses.

The pump-probe setups make it possible to study very rapid phenomena, for example the dynamics of electrons in matter, the diffusion of heat on a small scale or even ultra-rapid photo-acoustic phenomena, also called. "picosecond acoustics", This photo-acoustic application is very widely used in the industrial world. The company Rudolph Technologies has for many years marketed equipment for the in-line monitoring of the thickness of the layers of integrated circuits, very widely used by all the major microelectronics producers. The company MENAPiC uses a variant of the photo-acoustic technique, which makes it possible to characterize materials.

The principle of these optical setups is to employ two optical sources, notably laser, or one optical source divided into two beams. The first optical source, called "pump", is responsible for generating the phenomenon. The pump beam is focused on the sample through a dedicated focusing optic, such as a lens or a microscope objective for example. The second beam, called "probe", is also focused on the sample at the same point, with the same optic or a different optic.

The two beams have different optical trajectories but at least one of them is adjustable in length so that there is a means for making the lengths of the optical paths traveled by the two beams strictly equal. The adjustment of the length of one of the trajectories, by a delay line, sets the temporal phase-shift between the pump and probe beams and determines the instant at which the state of the sample is observed.

The two pump and probe beams are reflected on the sample or pass through it. The reflected or transmitted probe beam is analyzed in amplitude, phase or direction depending on the setups. The analysis of the dependencies of one of these quantities as a function of the delay between the pump and probe beams makes it possible to reconstruct the history of the sample before, during and after the creation of the phenomenon.

FIG. 1 represents an example of pump-probe optical setup 51 employing a single laser source 52. The beam $f_i$ deriving therefrom is divided into two beams, pump $f_p$ and probe $f_s$, by a splitter element 53. The delay between these beams is adjustable using a delay line 54, consisting in this example of a mirror that is movable according to a linear displacement. The two pump $f_p$ and probe $f_s$, beams are then recombined on the sample to be analyzed 100 using a focusing optic 55, unique for the two beams in the example considered. The probe beam $fs_r$ reflected by the sample 100 is analyzed, in this example, in intensity using a photodiode 56, the pump beam $f_p$, being stopped by a light trap 57.

The accurate adjustment of the distance between the focusing optic and the surface of the sample to be analyzed is crucial to obtaining the signal sought, as explained in the articles by A. Devos et al. "Strong oscillations detected by picosecond ultrasonics in silicon: evidence for an electronic structure effect", Physical Review B, 70, 12, 125208, 2004, and "A different way of performing picosecond ultrasonic measurements in thin transparent films based on laser-wavelength effects", Applied Physics Letters 86, 21, 211903, 2005.

On each change of sample or of area of the sample analyzed, in particular for a sample of variable thickness, this adjustment must be repeated according to the local thickness and the type of sample.

In known methods, the refocusing is performed by observing the trend of the signal when the focal distance varies, by seeking to obtain, with the new sample, a response comparable to or stronger than that of the reference sample. However, in the case of a sample having a weaker response, there is no guarantee of this exploration being sufficient. In practice, when it is necessary to modify the spatial superimposition of the beams, or the ratings of the electronic measurement apparatuses, the signal is often lost.

Another known technique consists in analyzing the divergence of the beam reflected on the sample. However, this technique is applicable only for the setups where the focusing and the re-collimation of the beams is performed by the same optic. When observing the reflected beam in the distance, the latter should appear collimated when the sample is, in the focal plane of the optic. This technique often suffers from a lack of accuracy.

In other known methods, an external system is used, for example an electronic system as described in the patent application CA 02281747, The method may rely on a measurement of capacitance, as in the Autofocus Control Module product from the company American Laser Enterprises. The method may also rely an optical measurement, using an external optical system, as in the product Focus-Trac™ from the company Motion X corporation.

The systems using capacitance measurements require a metal sample surface, which excludes all kinds of samples, like samples of glass for example.

The external optical systems demand the addition of different optics on the trajectory of the laser source, which is damaging for the accuracy of the measurements.

There consequently remains a need to further improve the methods making it possible to focus beams on an optically reflecting support in an optical setup, in order to remedy the above drawbacks.

The aim of the invention is to address this need and it achieves this, according to one of its aspects, by virtue of a method for refocusing an optical setup on a target surface, using at least one beam originating from a short-pulse optical source, comprising at least one optic for focusing the beam on the target surface, the refocusing being applied after knowing reference conditions for which the optical setup is considered to be focused, method in which:

- a focusing signal is detected that is representative of a temporal overlapping of the pulses between a beam reflected by the target surface and a reference beam not reflected by the target surface and deriving from the source, one of the beams being delayed by a delay line,
- based on said reference conditions, the optical path of the beam on which the delay line is placed is made to vary so as to cause said focusing signal to reach or exceed a predefined threshold, and
- the focusing is readjusted on the basis of the knowledge of the variation of optical path between the reference conditions and the conditions for which the focusing signal reaches or exceeds said predefined threshold.

The method according to the invention may be applied to the analysis of a sample defining said target surface, using a probe beam and a pump beam, of which at least one originates from the short-pulse optical source, comprising at least one delay line placed on the trajectory of one of the beams, and at least one optic for focusing the pump and probe beams on the sample to be analyzed, the focusing signal representative of the temporal overlapping of the pulses being detected between a beam reflected by the sample, delayed by the delay line, and a reference beam not reflected by the sample.

The invention relates also, according to another of its aspects, to a refocusing device intended to implement the method according to the invention above, the optical setup using at least one beam originating from a short-pulse optical source, comprising at least one optic for focusing the beam on the target surface,
the device comprising a means for detecting a focusing signal representative of a temporal overlapping of the pulses between a beam reflected by the target surface, and a reference beam not reflected by the target surface and deriving from the source, one of the beams being delayed by a delay line,
the device being configured to:
  vary, based on reference conditions for which the optical setup was considered to be focused, the optical path of the beam on which the delay line is placed so as to cause said focusing signal to reach or exceed a predefined threshold, and
  readjust the focusing based on the knowledge of the variation of optical path between said reference conditions and those for which the focusing signal reaches said predefined threshold.

The device according to the invention may be applied to the analysis of a sample defining said target surface, in which case the optical analysis setup advantageously uses a probe beam and a pump beam, of which at least one originates from the short-pulse optical source, comprises at least one delay line placed on the trajectory of one of the beams, and at least one optic for focusing the pump and probe beams on the sample to be analyzed, the focusing signal representative of the temporal overlapping of the pulses being detected between a beam reflected by the sample, delayed by the delay line, and a reference beam not reflected by the sample.

The invention makes it possible, notably in optical setups of the pump-probe type, to easily adjust the focusing of beams on a target surface, very rapidly, without the intervention of a technician or the use of external systems.

The method according to the invention makes it possible to automatically readjust the focusing successfully even for target surfaces defined by samples with a thickness differing by approximately 4 mm from that of the reference sample.

The invention may use the pump beam reflected on the surface where the focusing is required, a signal usually lost in this type of setup. The accuracy of the focusing is excellent because the temporal resolution is that of the pump-probe setup. The invention thus makes it possible to determine, independently of the response of the sample, the new position to be given to the focusing optic or optics.

The invention may be implemented using optics independent of the optical analysis setup, which avoids disturbing the latter, and a means making it possible to produce a cross-correlation, but does not require the addition of complex optical systems extraneous to the setup. The result of this is a very compact device.

The invention targets all equipment implementing an optical setup of pump-probe type, for example thermo-reflectance, picosecond acoustic or terahertz setups. It is particularly suited to rapid optical measurements and to acoustic analysis systems, for example for measurements of thickness, of lifetime of carriers in semiconductors, or of material elastic properties, notably for sonar applications.

The invention is also suited for single-beam optical setups, notably in machining applications, because it makes it possible to provide very accurate focusing.

It is possible, based on said reference conditions, for the optical path of the beam on which the delay line is placed to be varied by moving the delay line relative to the target surface, which gives an optimal focusing result. In a variant, the optical path of the beam on which the delay line is placed is varied by moving the target surface relative to the delay line, notably using a mobile sample-holder on which the target surface is arranged.

The delay line is preferably placed on the path of the reference beam not reflected by the target surface. Since this path is naturally shorter and the device requires the optical trajectories to be equal, it is advantageous to place the delay line on this path because it inevitably elongates the optical trajectory. In a variant, the delay line is placed on the path of the beam reflected by the target surface.

The delay line and/or the target surface are thus advantageously moved in order to produce various detections of the focusing signal, until said focusing signal reaches or exceeds the predefined threshold.

This predefined threshold may be equal to zero, or better, is strictly greater than zero. The predefined threshold may depend on the width of the pulses, a threshold equal to zero possibly not being sufficient to easily produce the refocusing, notably for pulses of the order of the picosecond. This predefined threshold may be a function of the wavelength of the optical source or sources.

The focusing signal representative of the temporal overlapping of the pulses may be obtained by cross-correlation between the beam reflected by the target surface, delayed by the delay line, and the reference beam not reflected by the target surface and deriving from the or one of the sources.

The cross-correlation, or auto-correlation, between optical pulses, notably laser pulses, has been described in the article by Chong et al. "Autocorrection measurement of femtosecond laser pulses based on two-photon absorption in GaP photodiode", Applied Physics Letter volume 105, page 062111, 2014.

The focusing method according to the invention may be implemented using a control loop, which notably makes it possible to analyze a sample in its entirety totally automatically. The control loop may be programmed to perform the different steps of the refocusing method according to the invention as well as the analysis of the state of the sample, on each change of analysis conditions, notably in the case of a change of sample or of a change of observation area.

The optical setup in which the method according to the invention is implemented may comprise a splitter element for splitting the beam originating from the optical source in order to create the beam reflected by the target surface and the reference beam not reflected by the target surface.

In a variant, the optical analysis setup comprises a single optical source and a splitter element for separating the beam originating from the optical source in order to create the pump and probe beams. In a further variant, the optical analysis setup comprises two optical sources, respectively emitting the pump and probe beams. In the case where the optical analysis setup comprises two distinct optical sources, the latter may be synchronized by using dedicated electronics.

The delay line is advantageously placed on the trajectory of the pump beam.

The reference beam not reflected by the sample may be the pump beam not delayed by the delay line, or the probe beam or, in the case where the optical analysis setup comprises a single source and a splitter element, a beam deriving from the optical source captured before the splitter element.

The use of the pump beam not delayed by the delay line is preferred, because that makes it possible to obtain higher energy pulses, the beam not passing through, on its trajectory, optics likely to modify it.

The optical analysis setup in which the method according to the invention is implemented advantageously comprises a single focusing optic allowing the two pump and probe beams to be recombined on the sample. In a variant, the optical analysis setup comprises a different focusing optic for each pump and probe beam.

The focusing may be readjusted by moving the focusing optic or optics relative to the target surface. In a variant, the focusing is modified by moving the target surface relative to the focusing optic or optics, notably using the movement of the sample-holder on which the target surface is arranged.

Upon implementing the method according to the invention, when the focusing may be re-established, and in the case where the delay line has been moved to vary the optical path of the beam on which the latter is placed, the delay line is preferably replaced at the reference zero to obtain the signal and for example begin the analysis of the sample or the machining.

The reference conditions advantageously correspond to the state in which the focusing optic or optics are considered to be focused on a reference target surface, and may correspond to a reference length of the optical path between the delay line and the target surface.

Determination of this reference length $d_1$ may be performed conventionally with a reference target surface other than that to be used, or with the target surface but when observing a reference area other than the area of the target surface having to be used, for example on the surface of the sample or at a greater or lesser depth in its thickness in the case of the analysis of a sample.

According to a preferred embodiment of the invention, the length $d_2$ of the optical path between the delay line and the target surface, for which the focusing signal reaches or exceeds the predefined threshold is determined. It is then sufficient to readjust the focusing by moving the focusing optic or the target surface by a value dependent preferably on $d_2-d_1$, but that may be governed by a relationship other than between $d_2$ and $d_1$.

Thus, in the case where the optical setup is configured for the beam to pass several times through the delay line or lines, the readjustment is a multiple of this value $d_2-d_1$, namely, for example, 2k $(d_2-d_1)$, where k is the number of go and return passes.

The maximum shift as an absolute value concerning the position of the target surface, permitted by the optical analysis setup, has the value d, being for example between 0 and 25 mm. The delay line cannot be distant from the target surface by a value greater than $d_1+d$ or less than $d_1-d$. This movement of the delay line may correspond to a negative or positive delay, that is to say to a delay or to an advance.

The search for the focusing signal by cross-correlation is then performed advantageously on the basis of the value $d_1-d$, by progressively incrementing the optical path length.

The method according to the invention is particularly suited to samples comprising a stack of thin layers, notably metal, on a substrate, notably of silicon. The samples comprise, for example, a layer of aluminum, notably with a thickness equal to 10 nm, a layer of silicon nitride, notably with a thickness equal to 200 nm, and a layer of silicon, having the composition Al/SiN/Si, In the case of a sample to be analyzed, the focusing may be done on the surface of the sample or at depth, at a predefined distance from its surface.

The optical source is advantageously a short pulse laser, with pulses notably of between 10 fs and 10 ps. The lasers used are for example the Chameleon Ultra model or the MIRA model from the company Coherent, or the Mai Tai model from the company Spectra Physics.

These lasers advantageously deliver pulses with a duration of approximately 100 fs, tunable to wavelengths of between 680 nm and 1050 nm, corresponding to the near infrared. In the case of a single optical source, a frequency doubler, arranged, as appropriate, before or after the pump/probe splitter element, may be used in order to deliver, for example, pulses that may be tuned to wavelengths of between 350 nm and 520 nm, corresponding to the blue, without modifying the duration of the pulses.

The average power of the optical source or sources may be between a few mW and more than 100 mW, an attenuation at the input of the optical setup being able to be used if necessary. The more the optical source emits energy pulses, the more the cross-correlation measurements are easy to perform.

The means for detecting the focusing signal may comprise a nonlinear crystal, which provides a significant polarization, notably a crystal of beta barium borate (BBO). In order to detect the focusing signal, the two beams are combined in the nonlinear crystal, and the beam deriving from the sum of the photons deriving from the cross-correlation is detected using a photodiode.

In a variant, the means for detecting the focusing signal is a two-photon photodiode on which the two beams are focused, notably a two-photon photodiode Silicon carbide (SiC), gallium arsenide phosphide (GaAsP) or gallium phosphide (GaP). The use of a two-photon photodiode, notably of silicon carbide, is particularly advantageous in the case of applications using optical sources of different wavelengths, for example a wavelength for the pump beam situated in the near infrared, with a wavelength of between approximately 680 nm and 1050 nm, and that of the probe beam situated in the blue, with a wavelength of between approximately 350 nm and 520 nm.

The optical delay line may comprise a mirror and/or one or more total reflection prisms and/or a retro-reflector and/or an electro-optical modulator, notably borne by a mobile carriage. The choice of the type of delay line depends advantageously on the wavelength of the optical source or sources. A microcontroller may be present in the device to drive the movements of the delay line.

The optical delay line may be incorporated in the means for detecting said focusing signal. That makes it possible to have a compact device with minimum footprint, and limit the modifications of a known focusing optical setup, by adding the fewest possible elements.

If necessary, the delay line used to vary the optical path of the optical beam on which the latter is placed may be the same as that used to set the temporal phase shift between the pump and probe beams for the analysis of the sample, in a known manner, as described previously. In a variant, the device according to the invention comprises two distinct delay lines.

The invention also relates, according to another of its aspects, to an assembly, also called kit, intended to implement the refocusing method according to the invention, comprising:

the refocusing device according to the invention, as defined above, comprising at least one delay line and at least one optic for focusing the beams on the target surface, and a reference target surface for the prior determination of the reference conditions for which the optical setup is considered to be focused on the reference target surface.

The reference target surface may be defined by a reference sample comprising a metal layer, notably of aluminum, and at least one layer of another material, notably silicon or glass.

The reference target surface is preferably observed under normal incidence for the prior determination of said reference conditions.

The features described above for the focusing method and device apply to said assembly.

Figure 2:
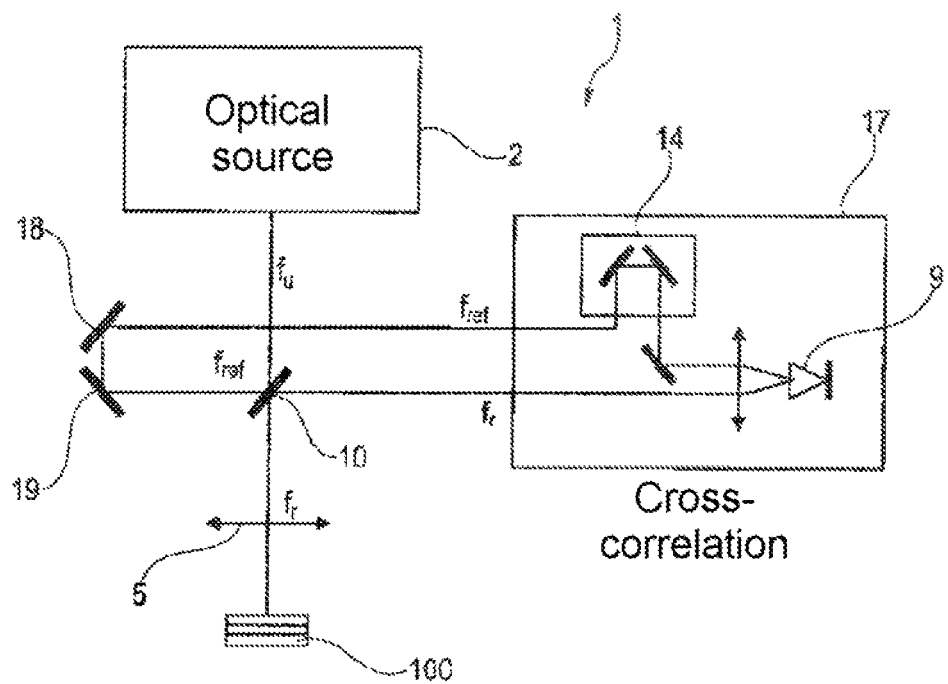
Figure 4:
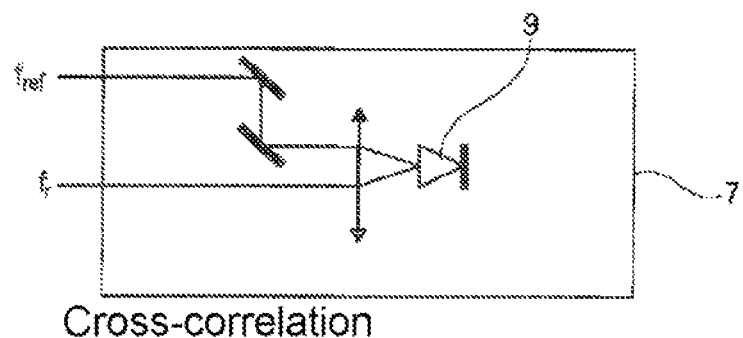
Figure 3:
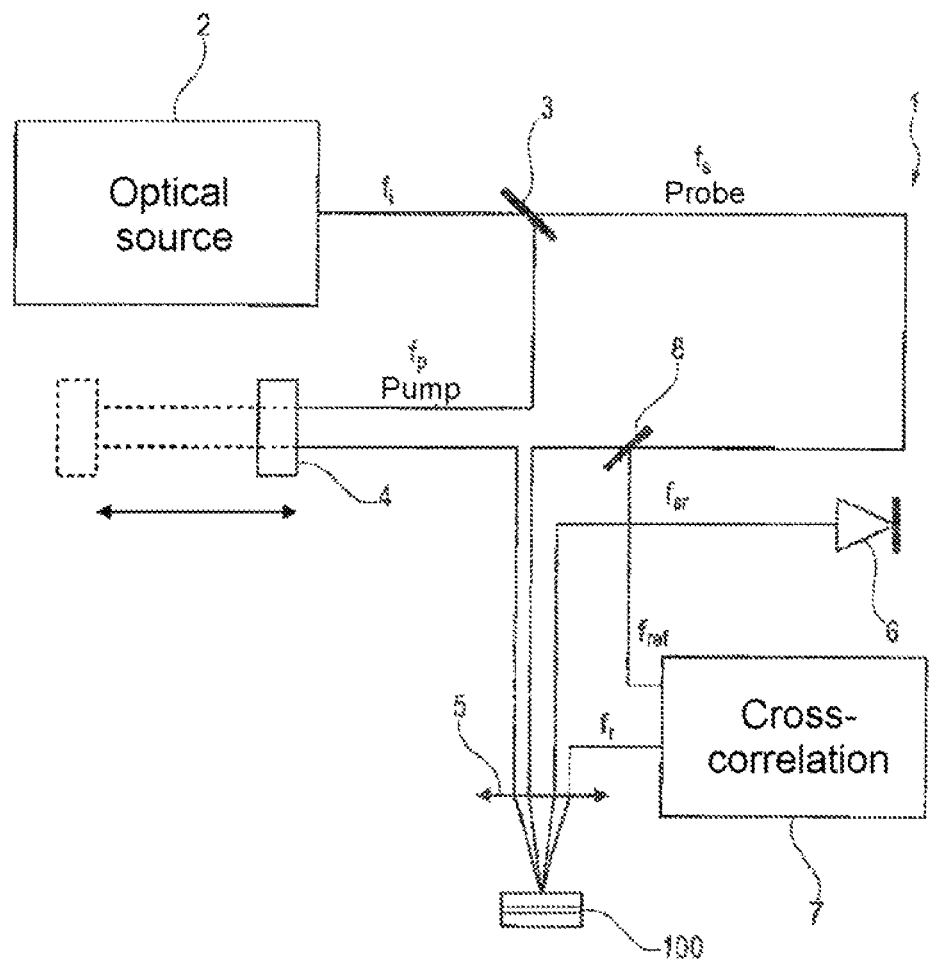
Figure 5:
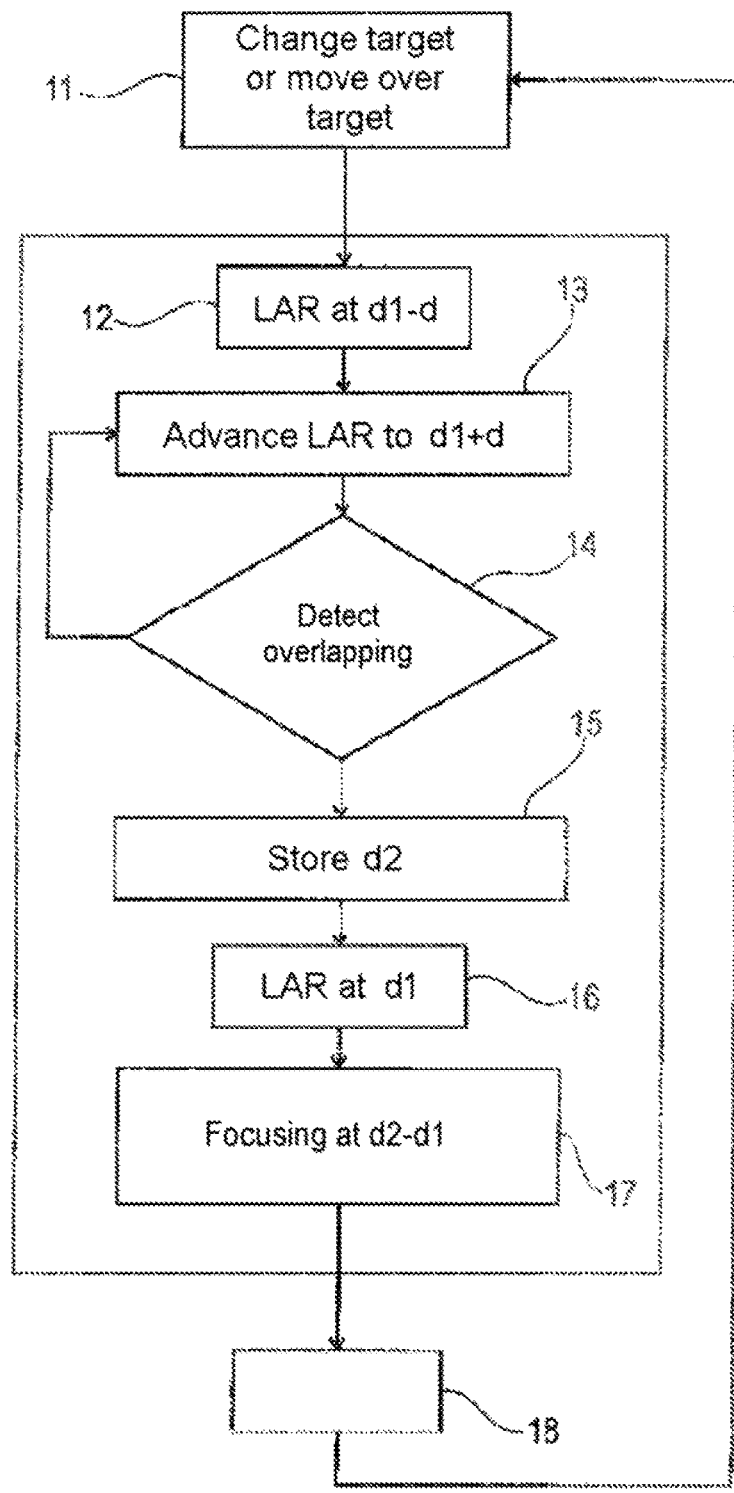
Figure 6:
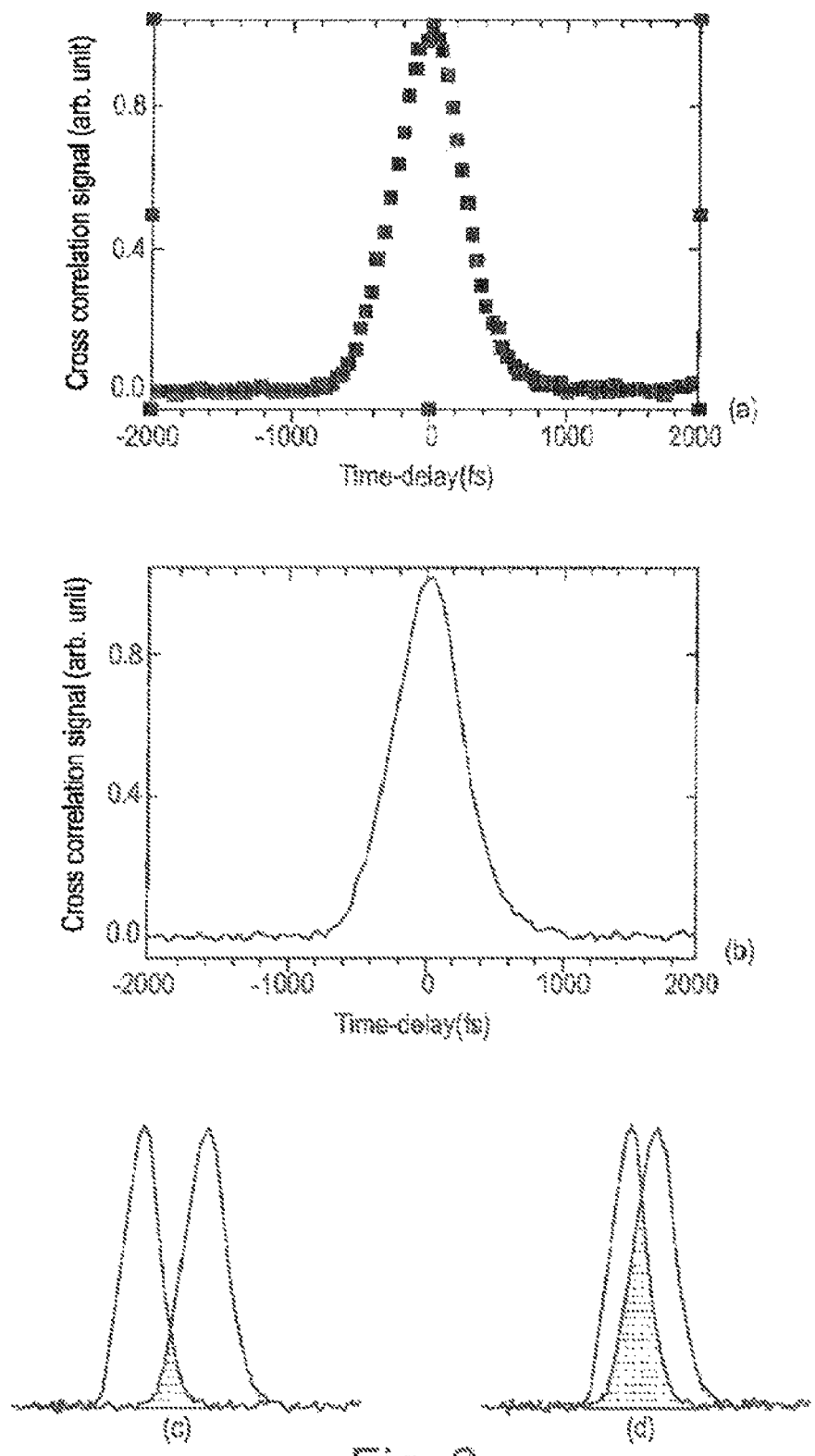

The invention will be able to be better understood on reading, the following detailed description, of nonlimiting exemplary implementations thereof, and on studying the attached drawing, in which:

FIG. 1, already described, represents a pump-probe optical setup according to the prior art, FIG. 2 represents a device according to the invention for focusing an optical setup, FIG. 3 represents a device according to the invention for focusing a pump-probe optical setup, FIG. 4 represents the detection means according to the invention of the device of FIG. 3, FIG. 5 illustrates steps in implementing the method according to the invention, and FIG. 6 represents timing diagrams of signals obtained by applying the method according to the invention, A device 1 for focusing a target surface 100 of an optical setup, intended to implement the refocusing method according to the invention, is represented in FIG. 2.

The optical setup uses a beam $f_u$ originating from an optical source 2. The optical source 2 is advantageously a short pulse laser, for example with a duration substantially equal to 100 fs, and tunable to wavelengths of between 680 nm and 1050 nm, which corresponds to the near infrared.

The optical setup comprises an optic 5 for focusing the beam $f_u$ on the target surface 100, and a delay line 14, incorporated in a detection means 17 described hereinbelow.

Prior to the implementation of the refocusing method according to the invention, a reference length $d_1$ of the optical path between the delay line 14 and the target surface has been determined, in reference conditions in which the focusing optic 5 is considered to be focused on a reference target surface.

The prior determination of the reference length $d_1$ may be performed with a reference target surface other than that to be used, or with the target surface 100 but in a reference area other than that having to be targeted.

A reference beam $f_{ref}$ not reflected by the target surface 100 is obtained by the arrangement of a splitter element 10 to capture a part of the beam $f_u$ and send it to a means 17 for detecting a focusing signal, using mirrors 18 and 19. The beam $f_r$ reflected by the target surface 100 and deriving from the beam $f_u$ is also sent to the means 17 for detecting a focusing signal. The reference beam $f_{ref}$ is delayed by the delay line 14.

A device 1 for focusing an optical setup for analyzing a sample 100 defining a target surface, intended to implement the method according to the invention, is represented in FIG. 3.

The sample 100 comprises, for example, a layer of aluminum, with a thickness equal to 10 nm, a layer of silicon nitride, with a thickness equal to 200 nm, and a layer of silicon, having the composition Al/SiN/Si. The invention is not however limited to a particular type of sample to be analyzed.

The optical analysis setup uses a pump beam $f_p$ and a probe beam $f_s$ originating from an initial beam $f_i$ emitted by a single optical source 2 and split into two pump and probe beams by a splitter element 3. In a variant not illustrated, the optical analysis setup comprises two optical sources respectively emitting the pump $f_p$ and probe $f_s$ beams.

A frequency doubler, not represented, may be arranged after the splitter element 3 in order to deliver, for the probe, pulses that may be tuned to wavelengths of between 350 nm and 520 nm, corresponding to the blue, without modifying the duration of the pulses. The invention is not however limited to a particular type of optical source or to particular types of pump and probe beams.

The optical analysis setup comprises a delay line 4 placed on the trajectory of the pump beam $f_p$ and a focusing optic 5 making it possible for the two pump $f_p$ and probe $f_s$ beams to be recombined on the sample to be analyzed 100. In a variant not illustrated, the optical analysis setup comprises a different focusing optic for each pump $f_p$ and probe $f_s$ beam. The focusing optic or optics 5 are for example lenses of 50 mm AC254-50-B or 60 mm Achro MG type.

Prior to the implementation of the refocusing method according to the invention, a reference length $d_1$ of the optical path between the delay line 4 and the sample has been determined, in reference conditions in which the focusing optic 5 is considered to be focused on a reference sample.

The prior determination of the reference length $d_1$ may be performed with a reference sample other than that to be analyzed, or with the sample to be analyzed 100 but in a reference area other than that having to be analyzed.

A reference probe beam $f_{ref}$ not reflected by the sample 100 is obtained by the arrangement of a splitter element 8 to capture a part of the probe beam and send it to a means 7 for detecting a focusing signal. The probe beam $fs_r$ reflected by the sample 100 is captured, in the example described, by a photodiode 6.

As may be seen in FIGS. 2 and 4, the means 7, 17 for detecting the focusing signal is advantageously a two-photon photodiode, for example of silicon carbide (SiC), particularly advantageous in the case of a pump-probe setup, when the wavelengths of the pump $f_p$ and probe $f_s$ beams are different.

In some variants, the means 7 for detecting the focusing signal is a two-photon photodiode of gallium arsenide phosphide (GaAsP) or gallium phosphide (GaP), or comprises a nonlinear crystal, for example a crystal of barium beta borate (BBO). The invention is not however limited to a particular type of means for detecting said focusing signal.

In the examples described, the delay line 4, 14 comprises a mirror borne by a mobile carriage. In some variants, the delay line 4, 14 comprises one or more total reflection prisms and/or a retro-reflector and/or an electro-optical modulator.

A microcontroller electronic circuit, not represented, may be present to drive the movements of the different mobile elements of the optical setup, notably the delay line 4, 14.

The refocusing method according to the invention may be implemented automatically using a control loop, an example of which is represented in FIG. 5.

Upon a change of target surface or change of observed area, a change represented by the step 11 in FIG. 5, a new focusing of the optical setup is required.

The delay line 4, 14 is initially placed at the value corresponding to $d_1-d$, in the step 12. The value d is the maximum offset between the delay line 4, 14 and the target surface 100 permitted by the optical analysis setup, and d may be between 0 and 25 mm. The delay line 4, 14 is progressively moved from the position corresponding to the optical path $d_1-d$, in a step 13, in order to increase the optical path of the beam on which the delay line 4, 14 is placed.

On each movement increment, in a step 14, a detection of the focusing signal representative of a temporal overlapping of the pulses between the beam $f_r$ reflected by the sample 100, and the reference beam $f_{ref}$, not reflected by the sample 100, is performed. The length of the optical path is incremented by moving the delay line until a focusing signal above a predefined threshold is detected.

In a step 15, the corresponding length $d_2$ is stored. In a variant not illustrated, the target surface 100 is moved relative to the delay line 4, 14 in order to make vary the optical path of the beam, for example using a sample-holder on which the target surface is arranged.

The detection of the focusing signal is done advantageously, as described above, by the cross-correlation between the beam $f_r$ reflected by the sample 100, and the reference beam $f_{ref}$, not reflected by the sample 100.

In a step 16, the delay line 4, 14 is repositioned at the reference zero, which corresponds to the reference length $d_1$ of the optical path.

In a step 17, the focusing is readjusted by moving the focusing, optic 5 by a value $d_2-d_1$, such that the focusing optic is once again correctly focused on the target surface 100.

The focusing may be readjusted by moving the focusing optic 5 relative to the target surface 100 by the value $d_2-d_1$. In a variant, the focusing is readjusted by moving the target surface 100 relative to the focusing optic 5, for example by moving the sample-holder on which the target surface is arranged, the focusing optic 5 remaining fixed.

In the case where the optical setup is configured for one of the beams to pass several times through the delay line 4, 14, the focusing readjustment value depends on the number of go and return passes.

The analysis of the sample defining the target surface 100, or the machining of the target surface 100, may then begin in the step 18.

FIG. 6 represents timing diagrams of signals obtained by applying the method according to the invention in the case of an optical analysis setup of the pump-probe type.

The timing diagram 6(*a*) represents an example of focusing signals obtained by cross-correlation between the pump beam $f_r$ reflected by the sample 100 and delayed by the delay line 4, and a reference probe beam $f_{ref}$ not reflected by the sample 100. The timing diagram 6(*b*) represents a smoothed curve passing through the measured values.

The timing diagrams 6(*c*) and 6(*d*) represent different overlappings according to the movement of the delay line 4.

A kit comprising the refocusing device according to the invention and a reference sample for the prior determination of the reference conditions may be proposed.

The expression "comprising a" should be understood to mean "comprising at least one", unless specified otherwise.

The invention claimed is:

1. A method for refocusing an optical setup on a target surface, using at least one beam originating from at least one short-pulse optical source, the optical setup comprising at least one optic for focusing the at least one beam on the target surface, the method comprising, after reference conditions for which the optical setup is considered to be focused are determined:
    capturing (i) a beam reflected by the target surface and (ii) a reference beam not reflected by the target surface and deriving from the at least one short-pulse optical source, one of the beams (i) and (ii) being delayed by a delay line;
    obtaining a focusing signal that is representative of a temporal overlapping of pulses between the beams (i) and (ii);
    based on said reference conditions, varying an optical path of one of the beams (i) and (ii) on which the delay line is placed so as to cause said focusing signal to reach or exceed a predefined threshold; and
    refocusing the optical setup based on a variation of the optical path between the reference conditions and conditions in which the focusing signal reaches or exceeds said predefined threshold.

2. The method as claimed in claim 1, being applied to an analysis of a sample defining said target surface using a probe beam and a pump beam, at least one of the probe beam and the pump beam originating from the at least one short-pulse optical source, wherein:
    the optical setup comprises the delay line placed on a trajectory of one of the probe beam and the pump beam, and the at least one optic focuses the pump beam and the probe beam on the sample to be analyzed; and
    the focusing signal representative of the temporal overlapping of the pulses is obtained between the beam (i) that is reflected by the sample and delayed by the delay line, and the reference beam (ii) that is not reflected by the sample, the beam (i) corresponding to the pump beam.

3. The method as claimed in claim 2, wherein the optical setup comprises a single optical source and a splitter element for splitting the at least one beam originating from said single optical source in order to create the pump beam and the probe beam.

4. The method as claimed in claim 2, wherein the optical setup comprises two optical sources respectively emitting the pump beam and the probe beam.

5. The method as claimed in claim 2, wherein the delay line is placed on a trajectory of the pump beam.

6. The method as claimed in claim 2, wherein the reference beam (ii) not reflected by the sample is:
    the pump beam not delayed by the delay line,
    the probe beam, or
    in a case where the optical setup comprises a single optical source and a splitter element, a beam deriving from the single optical source captured before said splitter element.

7. The method as claimed in claim 1, wherein the optical path of one of the beams (i) and (ii) on which the delay line is placed is varied by moving the delay line relative to the target surface, or by moving the target surface relative to the delay line, using a mobile sample-holder on which the target surface is arranged.

8. The method as claimed in claim 1, wherein said predefined threshold is equal to zero.

9. The method as claimed in claim 1, wherein said predefined threshold is strictly greater than zero.

10. The method as claimed in claim 1, wherein the focusing signal representative of the temporal overlapping of the pulses is obtained based on a cross-correlation between the beam (i) and the beam (ii).

11. The method as claimed in claim 1, wherein the optical setup comprises a splitter element for splitting the at least one beam originating from the at least one optical source in order to create the beam (i) and the beam (ii).

12. The method as claimed in claim 1, wherein the optical setup is refocused by moving the at least one optic relative to the target surface, or by moving the target surface relative to the at least one optic, using a mobile sample-holder on which the target surface is arranged.

13. The method as claimed in claim 1, wherein the reference conditions correspond to a state in which the at least one optic is considered to be focused on a reference target surface, a reference length of the optical path between the delay line and the target surface being determined from said state.

14. The method as claimed in claim 13, wherein prior determination of the reference length is performed with a reference target surface other than that to be used, or with the target surface but at a reference point other than a point of the target surface having to be used.

15. The method as claimed in claim 1, wherein a length of an optical path between the delay line and the target surface for which the focusing signal reaches said predefined threshold is determined.

16. The method as claimed in claim 15, wherein the optical setup is refocused by a value dependent on a difference between said length and a reference length such that the at least one optic is focused on the target surface, the reference length being a length of an optical path between the delay line and the target surface being determined from a state in which the at least one optic is considered to be focused on a reference target surface.

17. The method as claimed in claim 1, wherein the temporal overlapping of pulses indicate a measure of a similarity between the beams (i) and (ii) as a function of a displacement of the beam (i) relative to the beam (ii).

18. A refocusing device for refocusing an optical setup on a target surface, said optical setup using at least one beam originating from at least one short-pulse optical source, the optical setup comprising at least one optic for focusing the at least one beam on the target surface, the refocusing device comprising:
means for, after reference conditions for which the optical setup is considered to be focused are determined:
capturing (i) a beam reflected by the target surface, and (ii) a reference beam not reflected by the target surface and deriving from the at least one short-pulse optical source, one of the beams (i) and (ii) being delayed by a delay line, and
obtaining a focusing signal that is representative of a temporal overlapping of pulses between the beams (i) and (ii),
wherein the refocusing device is configured to:
vary, based on the reference conditions, an optical path of one of the beams (i) and (ii) on which the delay line is placed so as to cause said focusing signal to reach or exceed a predefined threshold; and
refocus the optical setup based on a variation of the optical path between said reference conditions and conditions in which the focusing signal reaches said predefined threshold.

19. The device as claimed in claim 18, being applied to an analysis of a sample defining said target surface, wherein:
the optical setup uses a probe beam and a pump beam, at least one of the probe beam and the pump beam originating from the at least one short-pulse optical source;
the optical setup comprises the delay line placed on a trajectory of one of the probe beam and the pump beam, and the at least one optic focuses the pump beam and the probe beam on the sample to be analyzed; and
the focusing signal representative of the temporal overlapping of the pulses is obtained between the beam (i) that is reflected by the sample and delayed by the delay line, and the reference beam (ii) that is not reflected by the sample, the beam (i) corresponding to the pump beam.

20. The device as claimed in claim 18, wherein the means for capturing the beams (i) and (ii) and obtaining said focusing signal comprises a nonlinear crystal or a two-photon photodiode.

21. The device as claimed in claim 18, wherein said at least one optical source is a short pulse laser of between 10 fs and 10 ps.

22. The device as claimed in claim 18, wherein the delay line comprises a mirror, one or more total reflection prisms, a retro-reflector, and/or an electro-optical modulator, borne by a mobile carriage.

23. The device as claimed in claim 18, wherein the delay line is incorporated in the means for capturing the beams (i) and (ii) and obtaining said focusing signal.

24. An assembly intended to implement a method for refocusing a target surface of an optical setup, using at least one beam originating from at least one short-pulse optical source, the optical setup comprising at least one optic for focusing the at least one beam on the target surface, the method comprising, after reference conditions for which the optical setup is considered to be focused are determined:
capturing (i) a beam reflected by the target and (ii) a reference beam not reflected by the target surface and deriving from the at least one short-pulse optical source, one of the beams (i) and (ii) being delayed by a delay line;
obtaining a focusing signal that is representative of a temporal overlapping of pulses between the beams (i) and (ii);
based on said reference conditions, varying an optical path of one of the beams (i) and (ii) on which the delay line is placed so as to cause said focusing signal to reach or exceed a predefined threshold; and
refocusing the optical setup based on a variation of the optical path between the reference conditions and conditions in which the focusing signal reaches or exceeds said predefined threshold,
the assembly comprising:
the refocusing device as claimed in claim 18, comprising the delay line and the at least one optic for focusing beams on the target surface; and a reference target surface for a prior determination of said reference conditions for which the optical setup is considered to be focused on said reference target surface.

25. The assembly as claimed in claim 24, wherein the reference target surface is defined by a reference sample comprising a metal layer including aluminum, and at least one layer of another material including silicon or glass, and is observed under normal incidence for the prior determination of said reference conditions.

\* \* \* \* \*